United States Patent
Lian (10) Patent No.: US 11,001,810 B1
(45) Date of Patent: May 11, 2021

(54) SERUM-FREE HUMAN PLURIPOTENT STEM CELL CULTURE MEDIUM

(71) Applicant: Lancell AB, Stockholm (SE)

(72) Inventor: Xiaojun Lian, State College, PA (US)

(73) Assignee: Lancell AB, Stockholm (SE)

( * ) Notice: Subject to any disclaimer, the term of this patent is extended or adjusted under 35 U.S.C. 154(b) by 0 days.

(21) Appl. No.: 16/679,932

(22) Filed: Nov. 11, 2019

(51) Int. Cl.
| | |
|---|---|
| *C12N 5/071* | (2010.01) |
| *C12N 5/074* | (2010.01) |
| *C12N 5/0735* | (2010.01) |
| *C12N 5/00* | (2006.01) |

(52) U.S. Cl.
CPC ......... *C12N 5/0696* (2013.01); *C12N 5/0068* (2013.01); *C12N 5/0606* (2013.01); *C12N 2500/32* (2013.01); *C12N 2500/34* (2013.01); *C12N 2500/38* (2013.01); *C12N 2500/90* (2013.01); *C12N 2500/98* (2013.01); *C12N 2501/113* (2013.01); *C12N 2501/115* (2013.01); *C12N 2501/15* (2013.01); *C12N 2533/52* (2013.01)

(58) Field of Classification Search
None
See application file for complete search history.

(56) References Cited

U.S. PATENT DOCUMENTS

| | | |
|---|---|---|
| 9,644,186 B2 | 5/2017 | Chen et al. |
| 2018/0066227 A1 | 3/2018 | Amit et al. |
| 2019/0017014 A1 | 1/2019 | Mandalam et al. |

FOREIGN PATENT DOCUMENTS

| | | | | |
|---|---|---|---|---|
| WO | WO-2005065354 A2 | * | 7/2005 | ............ C12N 5/0607 |
| WO | WO-2013134378 A1 | * | 9/2013 | ............ C12N 5/0606 |
| WO | WO-2018130831 A1 | * | 7/2018 | ............ C12N 5/0604 |

OTHER PUBLICATIONS

Sigma Life Science, Cell Culture Manual p. 1-383, 2014, (Year: 2014).*
Thomson, J.A., et al., Embryonic Stem Cell Lines Derived from Human Blastocysts, Nov. 6, 1998, Science, vol. 282, pp. 1145-1147.
Takahashi, K., et al., Induction of Pluripotent Stem Cells from Adult Human Fibroblasts by Defined Factors, Cell, Nov. 30, 2007, vol. 131, pp. 861-872.
Yu, J., et al., Induced Pluripotent Stem Cell Lines Derived from Human Somatic Cells, Science, Dec. 21, 2007, vol. 318, pp. 1917-1920.
Ludwig, T.E., et al., Derivation of human embryonic stem cells in defined conditions, Nature Biotechnology, Feb. 2006, vol. 24, No. 2, pp. 185-187.
Lin, Tzu Ting, Defined and Xeno-Free Culture for Human Pluripotent Stem Cells, A Thesis in Bioengineering, The Pennsylvania State University, May 1, 2017, 47 pages.
Chen, G., et al., Chemically defined conditions for human iPS cell derivation and culture, Nat Methods, May 2011, vol. 8, No. 5, pp. 424-429.
Ludwig. T.E., et al., Drivation of human embryonic stem cells in defined conditions, Nature Biotechnology Brief Communications, Jan. 1, 2006, vol. 24, No. 2, pp. 185-187.
Ludwig, T.E., Feeder-independent culture of human embryonic stem cells, Nature Methods, Aug. 24, 2006, vol. 3, No. 8, pp. 637-646.
Dakhore, S., et al., Human Pluripotent Stem Cell Culture: Current Status, Challenges, and Advancement, Stem Cells International, 2018, 7396905, 17 pages.
Chin, A., et al., Defined and Serum-Free Media Support, Undifferentiated Human Embryonic Stem Cell Growth, Stem Cells and Development, 2010, vol. 19, No. 6, pp. 753-761.

* cited by examiner

*Primary Examiner* — Anoop K Singh
*Assistant Examiner* — Magdalene K Sgagias
(74) *Attorney, Agent, or Firm* — Hodgson Russ LLP (57) ABSTRACT

Provided is a cell culture medium comprising enriched basal media supplemented with ascorbic acid, a member of the fibroblast growth factor (FGF) superfamily, a transforming growth factor-beta (TGF-beta) superfamily ligand, and a stable glutamine source. Methods of culturing stem cells in such culture medium for extended periods of time, populations of stem cells, and kits are also provided.

23 Claims, 7 Drawing Sheets

SERUM-FREE HUMAN PLURIPOTENT STEM CELL CULTURE MEDIUM

FIELD OF THE DISCLOSURE

The present invention relates to a cell culture medium for proliferation and/or long-term maintenance of pluripotent stem cells.

BACKGROUND OF THE DISCLOSURE

Stem cells, such as embryonic stem cells (ESCs) and induced pluripotent stem cells (iPSCs) offer tremendous promise in disease modelling, tissue engineering and cell-based therapies because of their unique combination of two properties—pluripotency and a high proliferative capacity. However, to date, the therapeutic potential of these cells has remained largely unrealized.

The utilization of stem cells in translational biomedical research requires a number of major technical hurdles to be overcome. Particular challenges are the development of efficient methods for stem cell expansion under chemically-defined and cost-effective conditions, and the production cost of clinical-grade stem cells (which is several orders of magnitude higher than other types of human cells). Significant costs are associated with special coating matrices and growth media involved in stem cell expansion, and special growth media typically cost in the range of 400-1000% the cost of the matrix.

The first human embryonic stem cell (hESC) lines were derived from normal human embryos in 1998 by James Thomson (Thomson et al., Science 282, 1145-7 (1998)). Culture conditions comprised irradiated mouse embryonic fibroblasts (MEF) feeder layers and the 20% fetal bovine serum culture media. This culture method is labor-intensive, hard to scale up, and it is difficult to maintain hESCs undifferentiated consistently due to the undefined components from fetal bovine serum and MEFs.

Over the past decade, advances have been made in producing chemically defined hPSC media to enable the maintenance and expansion of hESCs and induced pluripotent stem cells (iPSCs) (Takahashi et al., Cell 131, 861-72 (2007); Yu et al., Science 318, 1917-20 (2007)) under feeder-free conditions. The first chemically defined feeder-free stem cell medium for hPSC culture, mTeSR1 medium (Ludwig et al., Nat. Biotechnol. 24, 185-7 (2006)), contained several addition components over basal medium. Subsequently, a simplified version of mTeSR1, Essential 8 (E8) medium (Chen et al., Nat. Methods 8, 424-9 (2011)), was developed to reduce the number of additional components. However, the rate of proliferation of the stem cells and material costs for the media in chemically defined media is still a limiting step in generation of large quantities of cells required for research with an eye toward clinical application. While efforts have continued to make the defined media even more simple and at a lower cost, the complex combinatorial effects of different components have so far have made the task of designing a growth medium that is fully chemically defined, and yet be capable of supporting rapid proliferation of stem cells without adversely affecting pluripotency challenging.

SUMMARY OF THE DISCLOSURE

In the present disclosure, we identified a unique combination of chemically defined components which are sufficient for culture of human embryonic stem cells and human induced pluripotent stem cells, herein together referred to as human pluripotent stem cells (hPSCs). The present combination of chemically defined components is sufficient for self-renewal and pluripotency maintenance hPSCs in long-term cultures. The medium may be referred to herein as the pluripotent stem cell medium (PSC medium or PSCM). The present medium is both effective for supporting human embryonic stem cells and induced pluripotent stem cells expansion. hPSCs cultured in the present PSCM media displayed at least two-times faster growth rate when compared to other commercially available media, such as mTeSR1 or E8. The hPSCs can be maintained in PSCM for long-term culture, such as more than 6 months, and the hPSCs still express high levels of pluripotency makers such as Oct4, Sox2 and/or Nanog.

The robust ability to culture both human embryonic stem cells and induced pluripotent stem cells in PSCM should facilitate the translational applications of human stem cell research.

The present disclosure provides a cell culture medium that is suitable for long term culture and maintenance of human pluripotent stem cells in an undifferentiated state under serum-free, feeder-cell free conditions. The medium comprises a basal media such as DMEM or other similar media, enriched with components from F12, further supplemented with ascorbic acid, proteins such as lipid-rich albumin, transferrin, and insulin, glutathione, ammonium metavanadate, manganous chloride, sodium selenite, and ethanolamine, stable glutamine source, FGF, and TGF-beta.

The present disclosure also provides a method of culturing and proliferating human pluripotent stem cells under serum-free, feeder cell-free conditions for extended periods of time. The disclosure also provides a method of rapidly generating large populations of human pluripotent stem cells under chemically defined culture conditions.

BRIEF DESCRIPTION OF THE FIGURES

FIG. 1C shows hPSC stability in PSCM with respect to expression of pluripotency markers. After 30 passages in PSC media, hPSCs continue to display pluripotency markers such as Nanog and Oct4 via flow cytometry analysis. Compared to H9 cells cultured in mTeSR1, cells cultured in PSCM express Nanog levels approximately 10 times higher, even after 30 passages. Oct4 is shown in Y-axis and Nanog is shown in X-axis.

FIGS. 1E and 1F show hPSC stability in PSCM as seen by immunostaining. Immunostaining of Oct4, Nanog and Sox2 expression in H9 cells was performed, and H9 cells cultured in PSCM were positive for all the three pluripotency markers (FIG. 1E). We also performed immunostaining of pluripotency markers in human iPSCs 19-9-11 and found that human iPSCs are also positive for all the three pluripotency markers (FIG. 1F).

DESCRIPTION OF THE DISCLOSURE

The present disclosure provides an improved cell culture medium for proliferation and/or maintenance of human pluripotent stem cells. The medium can support feeder-cell independent, serum-free culture of human pluripotent stem cells for many passages. The medium is a chemically defined medium and comprises amino acids, inorganic salts, vitamins, proteins, reducing agents, trace elements, energy source, such as glucose and sodium pyruvate, lipids, ethanolamine, hypoxanthine, phenol red, putrescine and thymidine, a member of the FGF superfamily, a member of the TGF-beta superfamily, and a stable glutamine source. The concentration of ascorbic acid in the medium is at least 0.1 mM. In an embodiment, the medium does not contain one or more of gamma amino butyric acid (GABA), pipecolic acid (PA), and lithium (Li). Human pluripotent stem cells may be cultured and proliferated in this medium long-term under serum-free conditions in an undifferentiated state maintaining their pluripotency without being ever exposed to feeder cells, or any conditioned media therefrom.

Some, but not all of the components of the present medium (i.e., amino acids, inorganic salts, vitamins, proteins, reducing agents, trace elements, energy source (e.g., glucose and sodium pyruvate), lipids, other components like ethanolamine, hypoxanthine, phenol red, putrescine and thymidine) are present in some commercially available media. For example, Advanced DMEM/F12 (available from Thermo Fisher Scientific, for example) provides some of the components. Advanced DMEM/F12 (ADF) usually requires at least some serum for supporting culturing of many somatic cells, and has not been used as a basal media for hPSC culture. However, in the present disclosure, it was surprisingly observed that by modifying ADF by increasing the amount of ascorbic acid and with the addition of certain other components, such as a member of the FGF superfamily, a member of the TGF-beta superfamily, and a stable glutamine source, the modified ADF was able to support long-term culturing and maintenance of pluripotent stem cells under fully defined, serum-free, feeder cell-free conditions.

An example of a medium that is currently used for stem cell cultures is mTeSR1. However, mTeSR1 requires gamma amino butyric acid (GABA), pipecolic acid (PA), and lithium (Li). In the present disclosure, it was observed that such additional components were not required for multiple and long-term passaging of pluripotent stem cells in the present medium. On the contrary, it was observed that by reducing the number of components, we were unexpectedly able to achieve a higher proliferation rate. Furthermore, human pluripotent stem cells cultured in the present medium express higher levels of pluripotency markers and display long-term pluripotency and karyotypic stability compared to cells cultured in mTeSR1 under identical conditions. For example, human pluripotent cells have a shorter doubling time compared to cells cultured in mTeSR1, and can be maintained and cultured in the present culture medium for long periods (e.g. for at least 6 or 12 months or longer), and the resulting pluripotent stem cells still retain high expression of pluripotency markers (such as Oct4, Sox2 and Nanog) and display karyotypical stability, as determined by G-bank karyotyping assay.

It was observed that the present cell culture medium allows cells to proliferate faster, for example, at least twice as fast (i.e. have a two-times faster growth rate) as compared to other commercially-available media, such as mTeSR1. Thus, the cell culture medium of the invention may enable twice the yield of pluripotent stem cells (or the same yield in half the time), effectively reducing the cost per cell by 50% (not accounting for the associated savings in labor). In a clinical-scale setting with high fixed costs for GMP-grade cell culture facilities, even-greater savings can be expected as large volumes of cells can be produced in a shorter time. Accordingly, the cell culture medium of the invention could dramatically reduce cell production costs, allowing more results to be created in a shorter amount of time at the same cost. For the stem cell field, it will allow resources to be utilized in a more effective way, lowering the threshold for developing clinical stem cell therapy.

As discussed herein, the cell culture medium of the present disclosure has fewer components than previously-described stem cell culture media. It will be apparent to a skilled person that having fewer components in a stem cell culture medium offers significant advantages in the ease and cost of manufacturing. In addition, however, by including only the presently identified essential components for sustaining cell growth and intact pluripotency, the risk of having unwanted and/or unknown effects from unnecessary components is also significantly reduced. In general, it is important to minimize or eliminate such effects, especially when the resulting cells are to be ultimately used in a clinical setting.

The term "stem cell" generally refers to a cell that on division faces two developmental options: the daughter cells can be identical to the original cell (self-renewal) or they may be the progenitors of specialized cell types (differentiation). The stem cell is therefore capable of adopting one or other pathway (a further pathway exists in which one of each cell type can be formed). Stem cells are cells which are not terminally differentiated and are able to produce cells of other types.

Embryonic stem cells are those cells isolated from the inner cell mass of the blastocyst, which is the stage of embryonic development when implantation occurs. It will be appreciated, however, that embryonic stem cells can also be isolated without destruction of an embryo, for example used the methods described in Chung et al (Cell Stem Cell 2: 1-5, 2008). Chung and colleagues reported the derivation of five human embryonic stem cell (hESC) lines without embryo destruction, and demonstrated that they share the same characteristics as other hESC lines, including expression of the same markers of pluripotency, self-renewing capacity, karyotype stability, and the ability to differentiate into derivatives of all three germ layers both in vitro and in teratomas.

Pluripotent stem cells are stem cells with the potential to make any differentiated cell in the body. Induced pluripotent stem cells are a type of pluripotent stem cell artificially derived from a non-pluripotent cell, typically an adult somatic cell, by inserting certain genes or other methods. (See, for example, Takahashi & Yamanaka (2006, Cell 126(4) 663)).

It will be appreciated that the pluripotent stem cells may be derived from any eukaryotic source. For example, they may be derived from a vertebrate source such as a mammal. For example, pluripotent stem cells may be derived from rat, mouse, rabbit or dog or non-human primate or human. In an embodiment, the pluripotent stem cells are human pluripotent stem cells, and so in an embodiment, the PSCs or ESCs or iPSCs are human PSCs or ESCs or iPSCs. The iPSCs may be derived from any suitable cell type, including lung, fibroblasts (e.g. skin fibroblasts), keratinocytes, blood progenitor cells, bone marrow cells, hepatocytes, gastric epithelial cells, pancreatic cells, neural stem cells, B lymphocytes, ES derived somatic cells, and embryonic fibroblasts.

By the term "member of the FGF superfamily" as used herein is meant any fibroblast growth factor (FGF). FGFs are heparin-binding proteins, and their interaction with cell-surface associated heparin sulfate proteoglycans have been shown to be essential for FGF signal transduction. In humans, 23 members of the FGF superfamily have been identified, all of which are structurally related signaling molecules (Finklestein and Plomaritoglou, 2001, Head Trauma: Basic, Preclinical and Clinical Directions. New York: Wiley pp. 165-187; Blaber et al, 1996 Biochemistry 35(7): 2086-94; Ornitz and Itoh, 2001 Genome Biology 2(3): reviews 3005.1-reviews 3005.12). Thus, in an embodiment, the member of the FGF superfamily is one of the 23 members of the FGF superfamily that have been identified in humans, FGF1 to FGF 23, or orthologues thereof from other species, e.g. mammalian species: Members FGF1 to FGF 10 all bind to fibroblast growth factor receptors (FGFRs) and so it is preferred if the member of the FGF superfamily is one that binds to a FGFR, such as any of FGF1, FGF2, FGF3, FGF4, FGF5, FGF6, FGF7, FGF8, FGF9 or FGF10. In an embodiment, the member of the FGF superfamily is FGF2 or FGF1. In a preferred embodiment, the member of the FGF superfamily is FGF2. In an embodiment, the FGF is one that has been thermostabilized compared to the wild type protein, such as the thermostable FGF1 described by Chen et al.

The amino acid sequences (and the nucleotide sequences of the cDNAs which encode them) of many members of the FGF superfamily are readily available, for example by reference to GenBank. It should be noted, also, that because the sequence of the human genome is substantially complete, the amino acid sequences of human FGFs can be deduced therefrom. Although the FGF may be derived from any source, it is preferred if it is from a eukaryotic source. It is preferred if it is derived from a vertebrate source such as a mammal. For example, the FGF may be derived from a human, a rat, mouse, rabbit or dog or non-human. The term "derived from" includes a situation where a cDNA or gene was originally obtained using genetic material from the source, but that the protein is expressed in any host cell subsequently. Thus, it will be apparent that a human FGF may be expressed in a non-human host cell, such as an insect cell or E. coli, but be considered to be human-derived. The member of the FGF superfamily may be expressed and purified using well known molecular biology and protein expression techniques. Alternatively, the member of the FGF superfamily may be sourced commercially, for example from PeproTech (Rocky Hill, N.J.) or Sigma.

The term TGF-beta as used herein means any TGF-beta including TGFβ1, TGFβ2, and TGFβ3. In an embodiment, the TGF-beta is TGF-beta-1. It will be appreciated that the TGF-betas can be expressed and purified using well known molecular biology and protein expression techniques. Alternatively, many are available commercially and so can be sourced directly (e.g. from PeproTech). In an embodiment, the TGF beta superfamily of ligands includes Activin, and Nodal. Examples of activins include Activin A, Activin B, and Activin AB. Nodal binds to activin A receptor, type IIB ACVR2B. It can then either form a receptor complex with activin A receptor, type IB (ACVR1B) or with activin A receptor, type IC (ACVR1C). In an embodiment, the TGF-beta ligand is not bone morphogenetic protein (BMP).

By the term "stable glutamine source" as used herein is meant any source of glutamine that cells can utilize when present in a growth medium. In general, free glutamine may be unstable and therefore a dipeptide comprising glutamine is preferred. For example, the glutamine source can be L-alanyl-L-glutamine, which is available commercially (such as from Thermo Fisher Scientific as GlutaMAX®).

The buffer system in the present culture medium is bicarbonate based. In other serum-free media developed for cultures, HEPES is considered necessary to compensate for the lack of serum. However, it was surprisingly observed that in the present medium, there was no need to add HEPES and the bicarbonate in the medium provided adequate buffering system under appropriate $CO_2$ environment (generally from 5 to 10%). Therefore, in an embodiment, the present culture medium does not contain HEPES.

It will be appreciated that the components of the cell culture medium of the invention may be present in any appropriate concentration to support the culture and passaging of cells for at least up to 6 months, or at least 50 passages under serum-free, feeder cell free conditions. Some examples of suitable concentration ranges are provided below.

In an aspect, this disclosure provides a chemically defined medium for in vitro cell culture comprising amino acids, inorganic salts, vitamins, energy source such as glucose and sodium pyruvate, proteins, lipids, reducing agent, ethanolamine, hypoxanthine, putrescine, thymidine, a member of the FGF superfamily, a member of the TGF-beta superfamily, and a stable glutamine source, wherein the concentration of ascorbic acid in the medium is at least 0.1 mM. In an embodiment, the culture medium does not contain one or more of gamma amino butyric acid (GABA), pipecolic acid (PA), and lithium (Li). In an embodiment, the medium also does not need, and in an embodiment, does not contain 2-mercaptoethanol, pluronic F-68, Tween 80, or any other pluronic or non-ionic detergent. The medium can be used for culturing pluripotent stem cells (PSCs), including embryonic stem cells (ESCs), and induced pluripotent stem cells (iPSCs). The PSC may be of human or non-human origin. Because PSC can be cultured in this media for at least 50 or at least 100 passages, the use of this culture medium is expected to have a dramatic impact in increasing the yield of PSC thereby reducing the cost of producing PSC (such as hPSCs and hPSC-derived cells), and should facilitate further translational applications of stem cell research.

In an embodiment, the invention provides a cell culture medium comprising, consisting essentially of, or consisting of Advanced DMEM/F12 (ADF), added ascorbic acid, a member of the fibroblast growth factor (FGF) superfamily, a transforming growth factor-beta (TGF-beta) superfamily ligand, and a glutamine source.

The cell culture medium of the invention is described further below and in the accompanying Examples. The media may be referred to herein as the PSC medium or PSC media, or PSCM.

In an embodiment, the present disclosure provides a stem cell culture medium comprising or consisting essentially of DMEM (or other similar basal media), Group I components (alanine, asparagine, aspartic acid, glutamic acid, proline, biotin, vitamin B12, cupric sulfate, ferric sulfate, magnesium chloride, sodium phosphate dibasic, zinc sulfate, hypoxanthine, linoleic acid, lipoic acid, putrescine hydrochloride, sodium pyruvate, and thymidine), Group II components (ascorbic acid phosphate, lipid-rich albumin (such as AlbuMAX™), transferrin (such as human transferrin, holo), insulin (such as recombinant, full chain), monosodium glutathione, ammonium metavanadate, manganous chloride, sodium selenite, and ethanolamine), and Group III components (L-alanyl-L-glutamine, ascorbic acid, FGF, TGF-beta), wherein the total concentration of ascorbic acid phosphate in the medium is at least 0.1 mM, and in one embodiment, is from 0.1-0.8 mM. In an embodiment, the medium does not contain one or more of HEPES, gamma amino butyric acid (GABA), pipecolic acid (PA), and lithium (Li), 2-mercaptoethanol, pluronic F-68, Tween 80, or any other pluronic or non-ionic detergent.

Group I components referred to herein are those that are present in DMEM/F12, but not in DMEM, Group II components referred to herein are those that are present in Advanced DMEM/F12 (ADF), but not in DMEM/F12, and Group III components referred to herein are those that are present in the present medium but not in ADF.

In an embodiment, the present disclosure provides a human pluripotent stem cell culture medium comprising or consisting essentially of DMEM/F12 (or other similar enriched media), Group II components (ascorbic acid phosphate, albumin (AbuMAX™) human transferrin (holo), insulin (such as recombinant, full chain), monosodium glutathione, ammonium metavanadate, manganous chloride, sodium selenite, and ethanolamine), and Group III components (L-alanyl-L-glutamine, ascorbic acid, FGF, TGF-beta), wherein the total concentration of ascorbic acid in the medium is at least 0.1 mM, and in one embodiment, is from 0.1-0.8 mM. In an embodiment, the medium does not contain one or more of, gamma amino butyric acid (GABA), pipecolic acid (PA), and lithium (Li), 2-mercaptoethanol, pluronic F-68, Tween 80, or any other pluronic or non-ionic detergent. In an embodiment, the medium does not contain all of the following: gamma amino butyric acid (GABA), pipecolic acid (PA), and lithium (Li), 2-mercaptoethanol, pluronic F-68, Tween 80, or any other pluronic or non-ionic detergent. The medium may or may not contain HEPES.

In an embodiment, the present disclosure provides a human pluripotent stem cell culture medium comprising or consisting essentially of Advanced DMEM/F12 (or other similar advanced media) and Group III components (L-alanyl-L-glutamine, ascorbic acid, FGF, TGF-beta), wherein the total concentration of ascorbic acid in the medium is at least 0.1 mM (equivalent to about 25 mg/L ascorbic acid phosphate), and in one embodiment, is from 0.1-0.8 mM (equivalent to about 25 mg/L to 200 mg/L ascorbic acid phosphate). In an embodiment, the medium does not contain one or more of HEPES, gamma amino butyric acid (GABA), pipecolic acid (PA), and lithium (Li), 2-mercaptoethanol, pluronic F-68, Tween 80, or any other pluronic or non-ionic detergent. In an embodiment, the medium does not contain all of the following: HEPES, gamma amino butyric acid (GABA), pipecolic acid (PA), and lithium (Li), 2-mercaptoethanol, pluronic F-68, Tween 80, or any other pluronic or non-ionic detergent.

In an embodiment, the cell culture medium of the present disclosure comprises 0.1-0.8 mM ascorbic acid or salt or ester thereof as described above. For example, the cell culture medium may comprise 0.08-0.6 mM or 0.1-0.5 mM, or 0.1-0.4 mM, or 0.2-0.5 mM, or 0.2-0.4 mM, or 0.15-35 mM, or 0.2-0.3 mM, or 0.2-0.25 mM ascorbic acid, or a salt or ester thereof. In an embodiment, the cell culture medium comprises 0.2-0.25 mM ascorbic acid or a salt or ester thereof, such as around 0.24 mM.

In an embodiment, the cell culture medium of the invention comprises 25-75 µg/L of a member of the FGF superfamily, including any of those described above such as FGF1 and FGF2. For example, the cell culture medium may comprise 30-70 µg/L or 35-65 µg/L, of a member of the FGF superfamily (e.g. FGF2 and FGF1). In an embodiment, the cell culture medium comprises 40-60 µg/L of a member of the FGF superfamily (e.g. FGF2 and FGF1), such as around 50 µg/L.

In an embodiment, the cell culture medium of the invention comprises 0.75-2.25 µg/L of a TGF-beta superfamily of ligands, including any of those described above such as TGF-beta 1. For example, the cell culture medium may comprise 0.8-2.2 µg/L, or 0.9-2.1 g/L, or 1.0-2.0 µg/L, or 1.1-1.9 µg/L, or 1.2-1.8 µg/L, or 1.3-1.7 µg/L of a TGF-beta superfamily ligand (e.g., TGF-beta 1). In an embodiment, the cell culture medium comprises 1.4-1.6 µg/L of a member of the TGF-beta superfamily (e.g., TGF-beta 1) such as around 1.5 g/L.

In an embodiment, the cell culture medium of the invention comprises 1-5 mM glutamine source. For example, the cell culture medium may comprise 1-4 mM or 2-5 mM or 1-3 mM or 3-5 mM glutamine source (e.g., L-alanyl-L-glutamine). In an embodiment, the cell culture medium comprises 2-4 mM glutamine source (e.g., L-alanyl-L-glutamine), such as 2-3 mM or around 2.5 mM glutamine source (e.g., L-alanyl-L-glutamine).

In an embodiment, the cell culture medium of the invention may comprise 0.1-0.6 mM ascorbic acid, 25-75 µg/L a member of the FGF superfamily (e.g., FGF2 or FGF1), 0.75-2.25 µg/L TGF-beta superfamily ligand (e.g. TGF-beta 1), and 1-5 mM glutamine source (e.g. L-alanyl-L-glutamine). For instance, the cell culture medium may comprise about 0.25 mM ascorbic acid, about 50 µg/L a member of the FGF superfamily (e.g., FGF2 or FGF1), around 1.5 µg/L TGF-beta superfamily ligand (e.g. TGF-beta 1), and about 2.5 mM glutamine source. In an embodiment, the cell culture medium of the invention comprises about 0.25 mM ascorbic acid, about 50 µg/L FGF-2, about 1.5 µg/L TGF-beta-1, and about 2.5 mM L-alanyl-L-glutamine.

In an embodiment, the cell culture medium of the invention comprises or consists essentially of all of the constituents listed in the Table 1 below (PSCM), and in embodiment, comprises all of the constituents listed in Table 1 at the corresponding concentration provided for each component in the table. In an embodiment, the components are present in a range of the amounts shown in Table 1. plus/minus 10%. For example, glycine may be present in the range of about 16.8 mg/L to 20.6 mg/L, insulin may be present in the range of about 9 to 11 mg/L, and so on. In embodiments, the medium may contain components at the indicated concentrations shown in Table 1 plus/minus 1 to 20%. For example, the medium may contain components at the indicated concentrations shown in Table 1 plus/minus 5, 10, 15 or 20%. In an embodiment, the medium does not contain one or more of HEPES, gamma amino butyric acid (GABA), pipecolic acid (PA), and lithium (Li), 2-mercaptoethanol, pluronic F-68, Tween 80, or any other pluronic or non-ionic detergent. In an embodiment, the medium does not contain all of the following: HEPES, gamma amino butyric acid (GABA), pipecolic acid (PA), and lithium (Li), 2-mercaptoethanol, pluronic F-68, Tween 80, or any other pluronic or non-ionic detergent.

TABLE 1

An embodiment of PSC medium

| Component | mg/L |
|---|---|
| L-alanyl glutamine | 543 |
| Ascorbic acid phosphate | 63.5 |
| FGF2 | 0.05 |
| TGFβ1 | 0.0015 |
| Glycine | 18.75 |
| L-Alanine | 4.45 |
| L-Arginine hydrochloride | 147.5 |
| L-Asparagine-$H_2O$ | 7.5 |
| L-Aspartic acid | 6.65 |
| L-Cysteine hydrochloride-$H_2O$ | 17.56 |
| L-Cystine 2HCl | 31.29 |
| L-Glutamic Acid | 7.35 |
| L-Histidine hydrochloride-$H_2O$ | 31.48 |
| L-Isoleucine | 54.47 |
| L-Leucine | 59.05 |
| L-Lysine hydrochloride | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine disodium salt dihydrate | 55.79 |
| L-Valine | 52.85 |
| Biotin | 0.0035 |
| Choline chloride | 8.98 |
| D-Calcium pantothenate | 2.24 |
| Folic Acid | 2.65 |
| Niacinamide | 2.02 |
| Pyridoxine hydrochloride | 2 |
| Riboflavin | 0.219 |
| Thiamine hydrochloride | 2.17 |
| Vitamin B12 | 0.68 |
| i-Inositol | 12.6 |
| Calcium Chloride ($CaCl_2$) (anhyd,) | 116.6 |
| Cupric sulfate ($CuSO_4$-$5H_2O$) | 0.0013 |
| Ferric Nitrate (Fe($NO_3$)$_3$•$9H_2O$) | 0.05 |
| Ferric sulfate ($FeSO_4$-$7H_2O$) | 0.417 |
| Magnesium Chloride (anhydrous) | 28.64 |
| Magnesium Sulfate ($MgSO_4$) (anhyd,) | 48.84 |
| Potassium Chloride (KCl) | 311.8 |
| Sodium Bicarbonate ($NaHCO_3$) | 2438 |
| Sodium Chloride (NaCl) | 6995.5 |
| Sodium Phosphate dibasic ($Na_2HPO_4$) anhydrous | 71.02 |
| Sodium Phosphate monobasic ($NaH_2PO_4$-$H2O$) | 62.5 |
| Zinc sulfate ($ZnSO_4$-$7H_2O$) | 0.864 |
| Lipid rich albumin | 400 |
| Transferrin | 7.5 |
| Insulin | 10 |
| Glutathione, monosodium | 1 |
| Ammonium Metavanadate | 3.00E−04 |

TABLE 1-continued

An embodiment of PSC medium

| Component | mg/L |
|---|---|
| Manganous Chloride | 5.00E−05 |
| Sodium Selenite | 0.005 |
| D-Glucose (Dextrose) | 3151 |
| Ethanolamine | 1.9 |
| Hypoxanthine Na | 2.39 |
| Linoleic Acid | 0.042 |
| Lipoic Acid | 0.105 |
| Phenol Red | 8.1 |
| Putrescine 2HCl | 0.081 |
| Sodium Pyruvate | 110 |
| Thymidine | 0.365 |

In an embodiment, the present cell culture medium may comprise one or more antibiotics, such as penicillin, or streptomycin, or a mixture thereof. The antibiotics penicillin and streptomycin are used to prevent bacterial contamination in cell cultures due to their effective combined action against gram-positive and gram-negative bacteria. A penicillin streptomycin mixture is marketed as Pen-Strep by Thermo Fisher Scientific.

In an embodiment, the cell culture medium of the invention may further comprise an inhibitor of apoptosis, for example, a ROCK inhibitor such as Y-27632 [(R)-(+)-trans-4-(1-Aminoethyl)-N-(4-Pyridyl) cyclohexanecarboxamide dihydrochloride, Y-27632 dihydrochloride] (Watanabe et al, *Nature Biotechnology* 25, 681-686 (2007)), which is commercially available, for example from Sigma Aldrich.

The cell culture medium of the present disclosure can be xeno-free, by which is meant that none of its components are derived from non-human animals, but one or more of its components may be derived from humans. As an example, a xeno-free version of PSCM can be produced by replacing AlbuMAX present in ADF with rice-derived human recombinant albumin (HRA) or human serum albumin (HSA). The HRA or HSA concentration in the PSCM may be optimized to support hPSC self-renewal. In the present disclosure, similar data was obtained with Albumax, and albumin from a human source, such as human serum albumin or HRA.

The present medium can be prepared by routine methods. If prepared in a liquid form, the components can be added to water. The components may also be provided as a powdered mixture, or in a lyophilized form.

The present cell culture medium can be used for proliferation, passaging and/or maintenance of pluripotent stem cells (PSCs), including embryonic stem cells (ESCs) and induced pluripotent stem cells (iPSCs). The cells may be hESCs: H1, H7, H9, H13, H14; iPSC lines: 19-9-11, 6-9-9, 19-9-7, available from WiCell (wicell.org).

Human pluripotent stem cells can be cultured and maintained in the present medium. Generally, cells are passaged when they are about 60-70% confluent, but they can be passaged at any desired confluency. For passaging, cells are dissociated generally by exposing to EDTA, trypsin or chymotrypsin or similar enzyme cocktails, separated from the substrate, separated from the medium (generally by sedimentation, low speed centrifugation or filtration), and replated on appropriate substrates and grown in the presence of the present medium.

Incubation conditions for cell cultures are known in the art. For example, the conditions typically include culturing at a temperature of from 32-40° C., for example, about 37° C. The $CO_2$ concentration is generally about 1 to 10%, for example, about 2 to 7%, or about 5% or any range or value between 1 and 10%. The oxygen tension is adjusted to generally to provide normoxic conditions and is preferably about 20%.

The cells may be cultured on suitable substrates. For example, suitable substrates include Matrigel, collagen IV, fibronectin, laminin, collagen, vitronectin, polylysine, iMatrix-511 and the like. These materials are commercially available and routinely used for cell culture. In examples, iMatrix-511 may be used at about 5 μg/ml, vibronectin can be used at about 10 μg/ml and Matrigel may be used at 80 μg/ml.

In an embodiment, the cells may be cultured as suspension cultures, without the need for a substrate. In suspension cultures, the cells are suspended in a culture medium, and allowed to grow in under the same conditions as substrate attached cultures. Cells are generally grown in shaker or spinner flasks or bottles. For subculturing, no enzymatic treatment is necessary for detaching the cells from the substrate. EDTA may be used to treat the cell clusters to generate smaller cell clusters. A portion of the cell suspension may be removed and diluted in a fresh batch of medium and allowed to grow.

In the present disclosure, it was observed that proliferation of human pluripotent stem cells was more rapid that in other known and commonly used culture media under similar conditions, such as, for example, in mTeSR1. Hence, in an embodiment, the cell culture medium of the invention is generally one in which hPSCs proliferate in the medium at least 1.5 times faster than the rate at which they proliferate in mTeSR1 medium under similar culture conditions, such as at least 2 times faster, 2.5 times faster, 3 times faster, 4 times faster or 5 times faster. A reference to culturing under similar conditions generally means that apart from the media, parameters such as the seeding density, growth matrix, incubation conditions, temperature, agitation, (all of which may have an influence on growth rate) are the same. In an embodiment, at least one of the pluripotency markers is expressed at at least twice the level of expression in cells cultured in mTeSR1 under similar culture conditions. In an embodiment, at least one of the pluripotency markers is expressed at at least ten times the level of expression in cells cultured in mTeSR1 under similar culture conditions.

Measuring the rate of proliferation of hPSCs may be done by any suitable method in the art, and generally involves assessing the number of cells at regular points over time. The cell number may be determined, directly, for example by microscopic or electronic enumeration, or indirectly, for example by the use of chromogenic dyes, incorporation of radioactive precursors (e.g., labelled nucleosides into DNA such as titrated thymidine) or measurement of metabolic activity of cellular enzymes. Any convenient method may be used. A convenient measure of rate of proliferation is doubling time. It is the time it takes for cells to double in number.

Human pluripotent stem cells can be maintained in long-term culture in the present medium under serum-free, feeder cell layer free, condition medium-free conditions, in an undifferentiated state for several months. For example, undifferentiated phenotype could be observed for at least 6 months. In an embodiment, undifferentiated phenotype is observed for at least 7, 8, 9, 10, 11 or 12 months, or longer.

Culturing of cells for extended period of time requires subculturing or passaging. hPSCs can be maintained in culture in the present medium by passaging for several passages. For example, the hPSCs may be passaged for 1 to at least 100 passages or more, such as, for example, 2, 5, 10, 15, 20, 25, 30, 35, 40, 50, 60, 70, 80, 90 and 100 or more.

Even after passaging cells for up to several passages, it was observed that the cells still maintained pluripotency and/or karyotypic stability. The exhibition of pluripotency of PSCs may be via exhibiting any one or more properties of the cells that are associated with pluripotency. The property may comprise a morphological characteristic, an immunohistochemical characteristic, a molecular biological characteristic, or it may comprise a biological activity. All or a substantial portion of the cells may retain the one or more properties. This may be 70% or more, 80% or more, 90% or more, 95% or more, 97% or more, 98% or more, 99% or more, or substantially 100% of the treated cells.

The hPSCs cultured in the present culture medium are expected to retain the capacity to differentiate into all three cellular lineages, i.e., endoderm, ectoderm and mesoderm. For example, hPSCs may be differentiated into cardiomyocytes, neural progenitors, and other cells. Pluripotency may be assessed by any suitable method in the art. For example, methods of induction of hPSCs to differentiate each of these lineages are known in the art and may be used to assay the capability of the cells to differentiate. Alternatively, pluripotency can be determined by assessing the expression of one or more pluripotency markers such as Oct4, Sox2, Nanog and/or TRA-1-61. The expression of one or more pluripotency markers can be assessed at one or more time points during the culture of the cells in the medium. Expression may be assessed using standard techniques in the art for measuring expression levels, including the assessment of nucleic acid (e.g., RNA) and/or protein levels. When the marker is a protein, the technique is typically based on an immunoassay. The antibody selective for the pluripotency marker of interest may itself be labeled, for example with a radioactive label or a fluorescence label or with an enzyme. Alternatively, and preferably, it is detected with a secondary antibody, which binds the antibody selective for the pluripotency marker which is labeled. Antibodies to pluripotency markers that are available from commercial sources may be used. Examples of other suitable methods include flow cytometry (FACS), histochemical staining, western blotting, enzyme linked immunoassay (ELISA). Flow immunocytochemistry may be used to detect cell surface markers, immunohistochemistry (for example, of fixed cells or tissue sections) may be used for intracellular or cell surface markers). Western blot analysis may be conducted on cell extracts, and ELISA may be used for cellular extracts or products secreted into the medium.

hPSCs cultured in the culture medium may retain a normal karyotype during or after propagation. A "normal" karyotype includes a karyotype that is identical, similar or substantially similar to a karyotype of a parent hPSC. For example, there should not be any gross anomalies such as translocations, loss of chromosomes, deletions, etc. The karyotype may be assessed by a number of methods, for example visually under optical microscopy. Karyotypes may be prepared and analyzed as described in McWhir et al (*Methods Mol Biol*, 331: 77-90, 2006), and Hewitt et al (*Stem Cells*, 25(1): 10-8, 2007). Cells may also be karyotyped using a standard G-banding technique (available at many clinical diagnostics labs that provides routine karyotyping services, such as the Cytogenetics Lab at Oakland Calif.) and compared to published hPSC karyotypes.

In an embodiment, the disclosure provides a cell culture medium comprising or consisting essentially of amino acids, inorganic salts, vitamins, trace elements, energy source selected from the group consisting of glucose, sodium pyruvate or a combination thereof, proteins, lipids, ethanolamine, hypoxanthine, putrescine, thymidine, a member of the FGF superfamily, a TFG-beta superfamily of ligands, and a stable glutamine source at concentrations sufficient to allow in vitro passaging of undifferentiated hPSCs for at least up to 50 passages under serum-free, feeder cell-free conditions, wherein the concentration of ascorbic acid phosphate in the medium is from 0.1-0.8 mM.

In an embodiment, the disclosure provides a cell culture medium comprising or consisting essentially of DMEM, alanine, asparagine, aspartic acid, glutamic acid, proline, biotin, vitamin B12, cupric sulfate, ferric sulfate, magnesium chloride, sodium phosphate dibasic, zinc sulfate, hypoxanthine, linoleic acid, lipoic acid, putrescine hydrochloride, sodium pyruvate, and thymidine, a source of ascorbic acid, lipid-rich albumin, transferrin, insulin, monosodium glutathione, ammonium metavanadate, manganous chloride, sodium selenite, and ethanolamine, L-alanyl-L-glutamine, a member of the FGF superfamily, a member of the TGF-beta superfamily of ligands, at concentrations sufficient to allow in vitro passaging of undifferentiated hPSCs for at least up to 50 passages under serum-free, feeder cell-free conditions, wherein the concentration of ascorbic acid in the medium is from 0.1-0.8 mM.

In an embodiment, the disclosure provides a cell culture medium comprising or consisting essentially of DMEM/F12, a source of ascorbic acid, lipid-rich albumin, transferrin, insulin, monosodium glutathione, ammonium metavanadate, manganous chloride, sodium selenite, and ethanolamine, L-alanyl-L-glutamine, a member of the FGF superfamily, a member of the TGF-beta superfamily of ligands, at concentrations sufficient to allow in vitro passaging of undifferentiated hPSCs for at least up to 50 passages under serum-free, feeder cell-free conditions, wherein the concentration of ascorbic acid in the medium is from 0.1-0.8 mM.

In an aspect, this disclosure provides a method for culturing and maintaining human pluripotent stem cells comprising growing/maintaining cells in the serum-free culture medium described herein, wherein the cells are not exposed to, and have not been exposed to feeder cells or conditioned medium therefrom. The cells may be maintained for at least 30 passages and express pluripotency markers such as one or more of Nanog, Oct4 and Sox2. In an embodiment, the pluripotency markers may be expressed at least twice the level of expression in cells cultured in mTeSR1 under similar conditions. In an embodiment, the pluripotency markers may be expressed at least five or ten times the level of expression in cells cultured in mTeSR1 under similar conditions.

In an aspect, the disclosure provides a kit comprising Advanced DMEM/F12 (ADF), a source of ascorbic acid, a member of the fibroblast growth factor (FGF) superfamily, a transforming growth factor-beta (TGF-beta) superfamily ligand, and a glutamine source. In an embodiment, the FGF in the kit is FGF2 or FGF1. In an embodiment, the TGF-beta is TGF-beta1. In an embodiment, the glutamine source is L-alanyl-L-glutamine. In an embodiment, all the components of the medium are pre-mixed and may be provided in a powdered form with instructions relating to preparation of the culture medium. The components may be provided in a sterile form. The kit may further comprise antibiotics such as penicillin and/or streptomycin, and gentamycin. The kit may also comprise an inhibitor of apoptosis such as a ROCK inhibitor (e.g. Y-27632).

In an embodiment, the disclosure provides a kit for preparing a cell culture medium comprising: i) DMEM, ii) a combination of alanine, asparagine, aspartic acid, glutamic acid, proline, biotin, vitamin B12, cupric sulfate, ferric sulfate, magnesium chloride, sodium phosphate dibasic, zinc sulfate, hypoxanthine, linoleic acid, lipoic acid, putrescine hydrochloride, sodium pyruvate, and thymidine, a source of ascorbic acid, lipid-rich albumin, transferrin, insulin, monosodium glutathione, ammonium metavanadate, manganous chloride, sodium selenite, and ethanolamine, L-alanyl-L-glutamine, a member of the FGF superfamily, a member of the TGF-beta superfamily of ligands, and iii) optionally, instructions for preparing the cell culture medium, wherein the components are provided at concentrations sufficient to allow in vitro passaging of undifferentiated hPSCs for at least up to several passages, such as 50 passages, under serum-free, feeder cell-free conditions, wherein after preparation of the cell culture medium, the concentration of ascorbic acid in the medium is from 0.1-0.8 mM.

In an embodiment, the disclosure provides a kit for preparing a cell culture medium comprising: i) DMEM/F12, ii) a source of ascorbic acid such as ascorbic acid phosphate, lipid-rich albumin, transferrin, insulin, monosodium glutathione, ammonium metavanadate, manganous chloride, sodium selenite, and ethanolamine, L-alanyl-L-glutamine, a member of the FGF superfamily, a member of the TGF-beta superfamily of ligands, and iii) optionally, instructions for preparing the cell culture medium, wherein the components are provided at concentrations sufficient to allow in vitro passaging of undifferentiated hPSCs for at least up to 50 passages under serum-free, feeder cell-free conditions, wherein after preparation of the cell culture medium, the concentration of ascorbic acid in the medium is from 0.1-0.8 mM, 0.0.15-0.7 mM, or 0.2-0.4 mM, or 0.15-0.3 mM.

In an embodiment, the disclosure provides a kit for preparing a cell culture medium comprising: i) Advanced DMEM/F12, ii) a source of ascorbic acid such as ascorbic acid phosphate, L-alanyl-L-glutamine, a member of the FGF superfamily, a member of the TGF-beta superfamily of ligands, and iii) optionally, instructions for preparing the cell culture medium, wherein the components are provided at concentrations sufficient to allow in vitro passaging of undifferentiated hPSCs for at least up to several passages, such as 50 passages, under serum-free, feeder cell-free conditions, wherein after preparation of the cell culture medium, the concentration of ascorbic acid in the medium is from 0.1-0.8 mM.

In an aspect, this disclosure provides a method of maintaining undifferentiated hPSCs in culture for extended periods of time under fully defined chemical conditions comprising culturing and passaging cells in the present medium under serum-free, feeder cell-free, condition medium from feeder cells-free conditions for several passages. The cells can be frozen at any passage and then thawed and passaging can be continued or the cells may be used for generating differentiated cells of any lineage as desired.

In an aspect, this disclosure provides a population of pluripotent stem cells that are cultured in the present medium under serum-free and feeder-cell layer free conditions. In an embodiment, the cells are human pluripotent stem cells.

The following examples further illustrate the invention and are not intended to be restrictive in any way.

Example 1

This example describes preparation of an embodiment of the PSC medium and the use of the medium for culture of human pluripotent stem cells.

Methods

Preparation of PSC Medium 6.25 ml GlutaMAX (Thermo Fisher Scientific), 305 µl ascorbic acid phosphate solution (100 mg/ml) (Sigma), 500

µl FGF2 solution (50 µg/ml) (Peprotech) and 500 µl TGFβ1 solution (1.5 µg/ml) (Peprotech) were added to 500 ml Advanced DMEM/F12 (Thermo Fisher Scientific).

Passage hPSC Colonies Cultured in PSC Media with EDTA (0.5 mM)

Matrigel-coated dishes equilibrated to room temperature were used. PSC medium was also equilibrated to room temperature. hPSCs growing on culture places (6-well plates) were detached by exposing to EDTA for about 3 minutes. The EDTA solution was removed and 3 ml of PSCM+5 µM Y27632 (a ROCK inhibitor) was added to each plate. When the cells were separated and rounded up, they were removed from the well. The contents of the well were pooled into a sterile conical tube containing 9 ml of PSCM+5 µM Y27632 and gently mixed to obtain a cell suspension. 2 ml of the cell suspension was added into each well of a new Matrigel-coated six-well plate (a split ratio of 1:6). The cells are then continued in culture. The medium was replenished the next day and new then every 3-3 days. When the cells reached about 80% confluency, they were split again.

Flow Cytometry Analysis

Cells were dissociated into single cells with Accutase® for 10 min and then fixed with 1% paraformaldehyde for 20 min at room temperature and stained with primary and secondary antibodies in PBS plus 0.1% Triton X-100 and 0.5% BSA. Data were collected on a FACSCaliber flow cytometer (Beckton Dickinson) and analyzed using FlowJo. FACS gating was based on the corresponding isotype antibody control. Oct4 and Nanog antibodies were used.

Immunostaining

Cells were fixed with 4% paraformaldehyde for 15 min at room temperature and then stained with primary and secondary antibodies in PBS plus 0.4% Triton X-100 and 5% non-fat dry milk. Nuclei were stained with Gold Anti-fade Reagent with DAPI. A Nikon epifluorescence microscope was used for imaging analysis. Antibodies used were Oct4 (Mouse IgG2b Clone: C-10 sc-5279 available commercially from Santa Cruz), Nanog (Nanog (D73G4) XP® Rabbit mAb #4903 from Cell Signaling Technologies) and Sox2 antibodies (Sox2 (D6D9) XP® Rabbit mAb #3579 from Cell Signaling Technologies).

Results

Increased Proliferation Rate

Figure 1A:
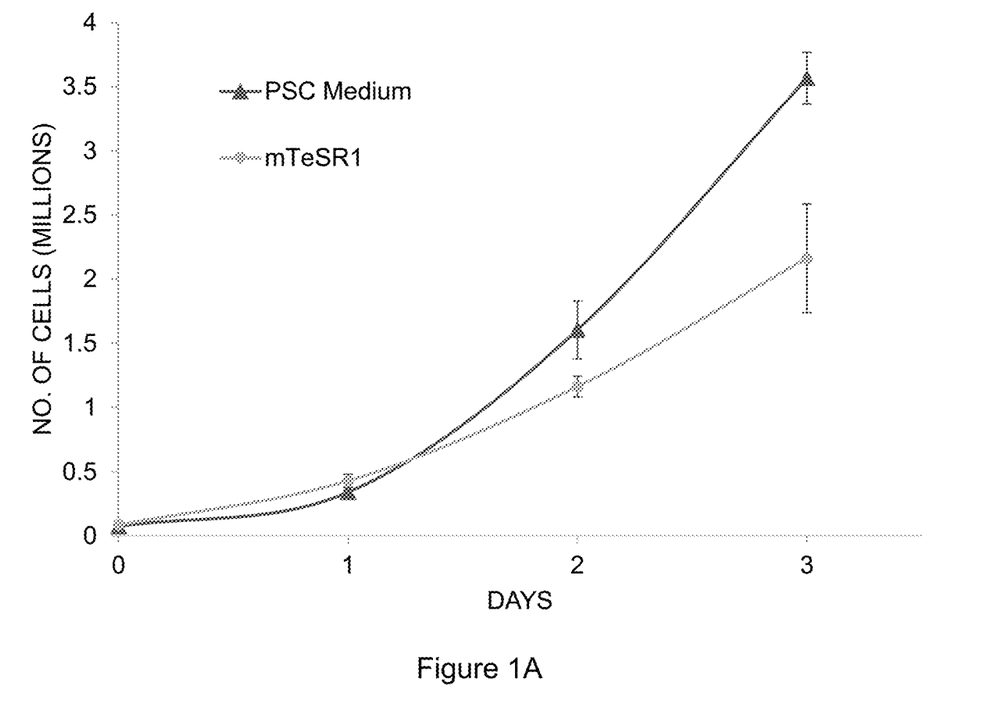
FIG. 1A shows proliferation of human pluripotent stem cells (hPSC) in the present media (PSCM) compared to mTeSR1 media. Human embryonic stem cell line H9 cultured in PSCM and mTeSR1 for 5 passages at the same seeding density and conditions, where cells cultured in PSCM display twice the cell count after the initial day of post-seeding adaption where cells display low proliferation in both mediums.
Figure 1B:
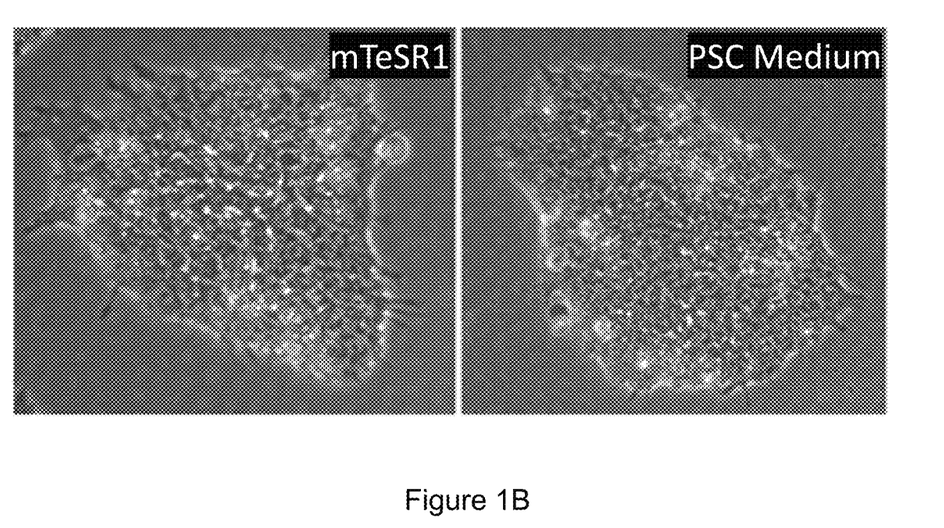
FIG. 1B shows hPSC morphology in PSCM. Morphology of cells cultured in PSCM and mTeSR1 are shown. Cells show similar morphology in both media indicative of pluripotency.

H9 cells cultured in PSCM compared to mTeSR1 for 5 passages with otherwise the same seeding density and conditions, display twice the cell count after the initial day of post-seeding adaption where cells display low proliferation in both mediums (FIG. 1A). Morphology of cells cultured in PSCM and mTeSR1 are shown in FIG. 1B.

Long-Term Stability

Figure 1C:
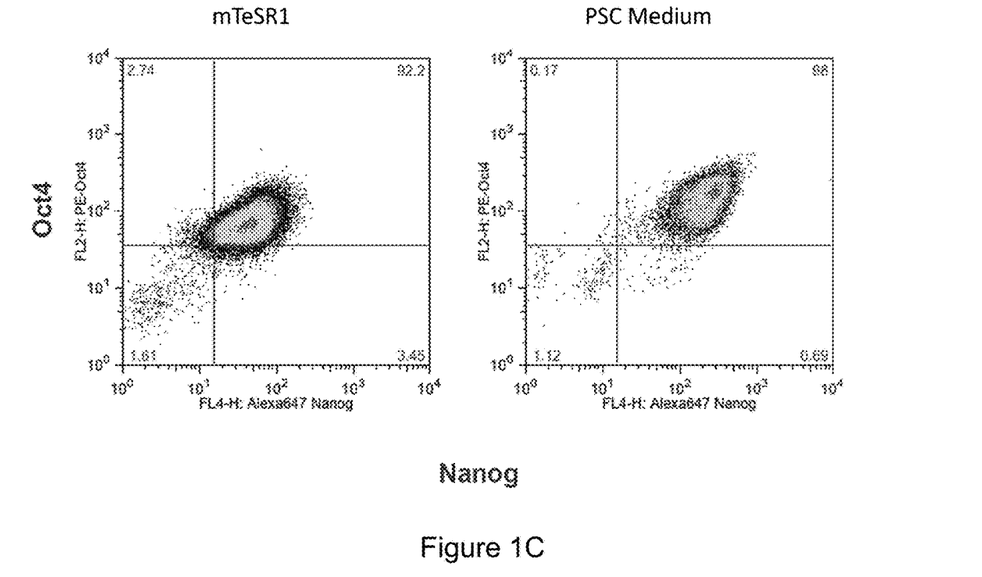
Figure 1D:
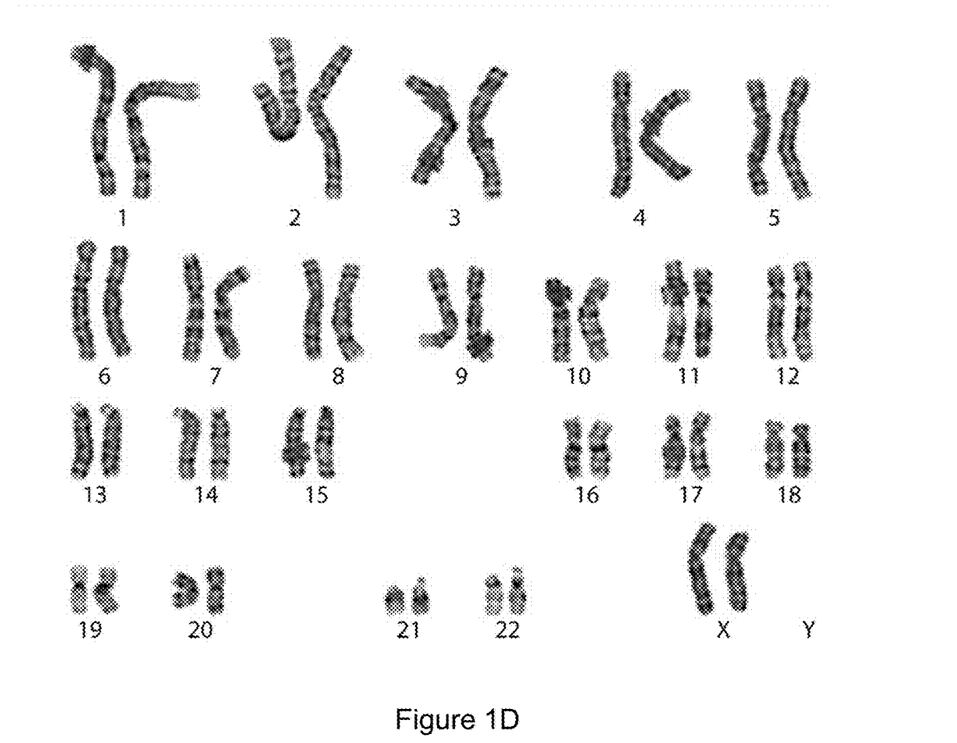
FIG. 1D shows hPSC stability in PSCM with respect to karyotyping. H9 cells cultured in PSCM for 30 passages display no chromosomal anomalies confirmed by karyotyping.
Figure 1E:
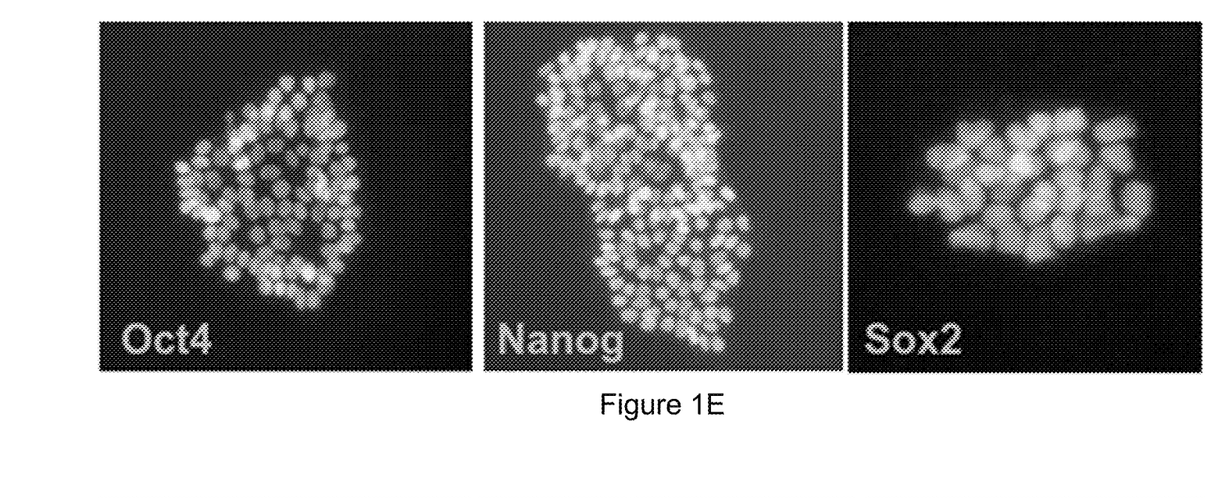
Figure 1F:
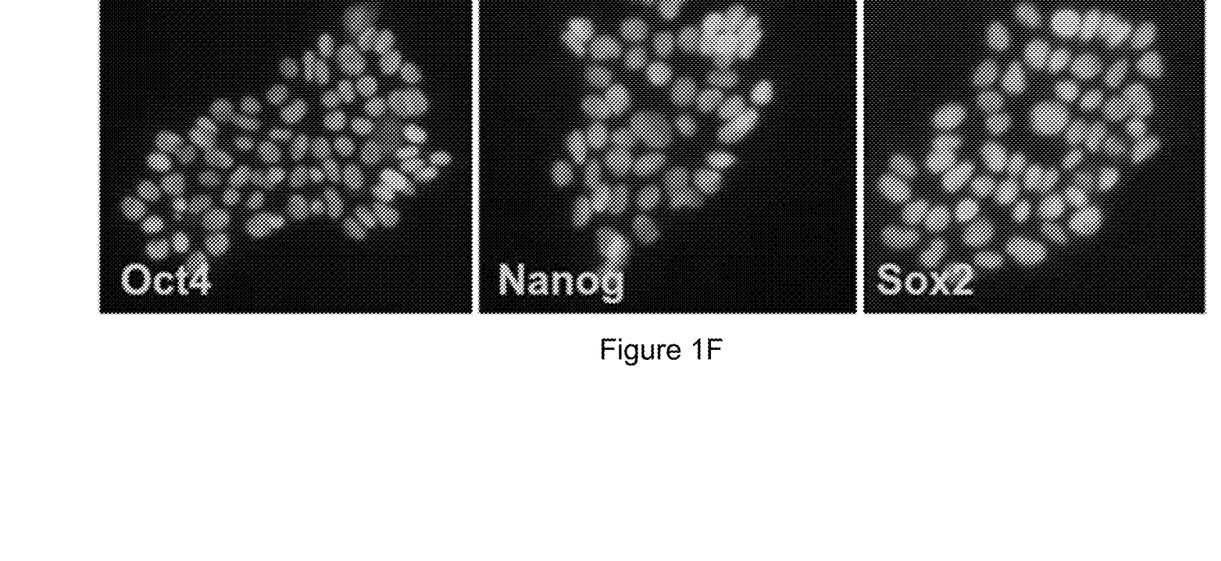

After 30 passages in PSC media, hPSCs continue to display pluripotency markers such as Nanog and Oct3/4 via flow cytometry analysis (FIG. 1C). Compared to H9 cells cultured in mTeSR1, cells cultured in PSCM express Nanog levels approximately 10 times higher, even after 30 passages (FIG. 1C). H9 cells cultured in PSCM for 30 passages display no chromosomal anomalies confirmed by karyotyping (FIG. 1D). Immunostaining of Oct4, Nanog and Sox2 expression in H9 cells was performed, and H9 cells cultured in PSCM were positive for all the three pluripotency markers (FIG. 1E). We also performed immunostaining of pluripotency markers in human iPSCs 19-9-11 and found that human iPSCs are also positive for all the three pluripotency markers (FIG. 1F).

Example 2

Figure 2:
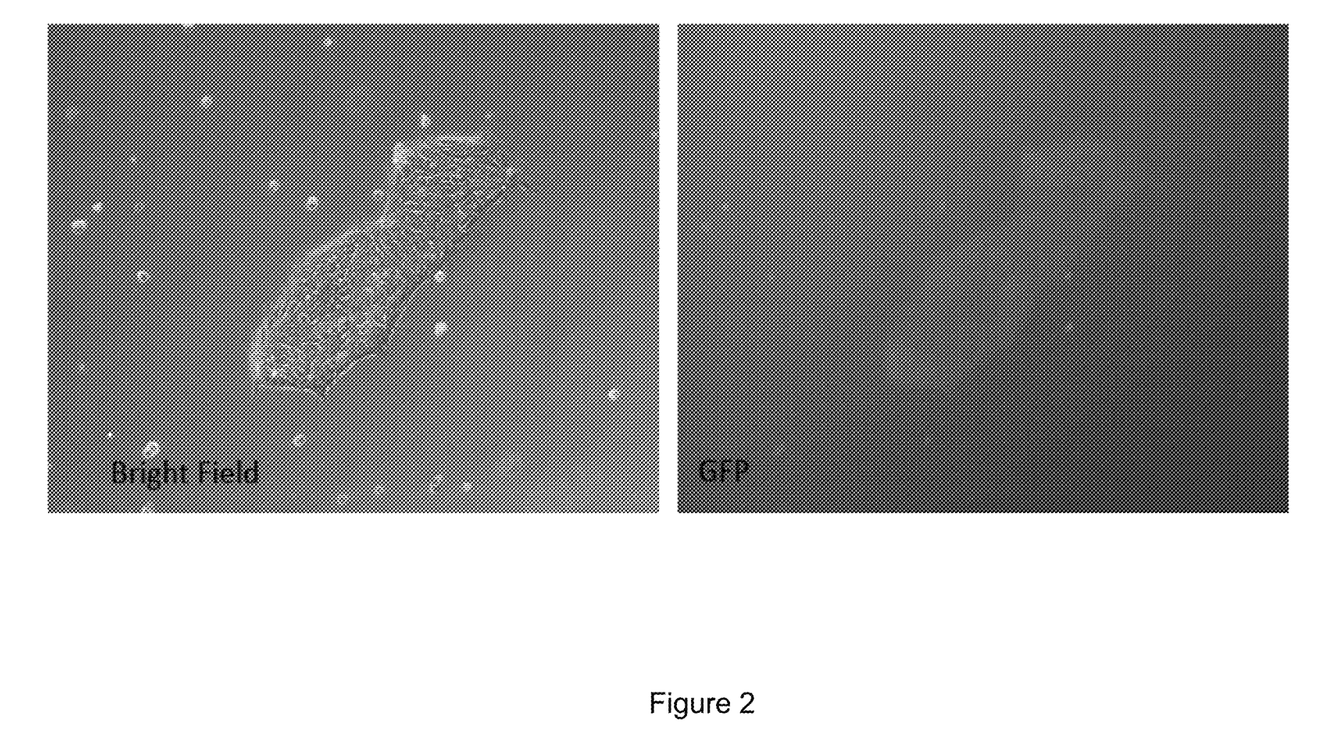
FIG. 2 shows H1Oct4-GFP cells cultured in PSCM for 10 passages. Microscope images of cell(s) with bright-field (left) and GFP (right), showing expression of GFP, and therefore showing expression of Oct4 in human embryonic stem cell line H1 cells after 10 passages in PSCM.

Human embryonic stem cell line H1-Oct4-GFP cells were cultured in PSC media containing L-alanyl-L-glutamine for 10 passages. As is evident from FIG. 2, after 10 passages we can still observe GFP expression. The expression of GFP is driven by a gene called Oct4 which is a stem cell pluripotency marker. Therefore, if a stem cell expresses Oct4, the stem cell is pluripotent. Since the cells express Oct4 driven GFP, they maintain pluripotency.

Example 3

In this example, we generated differentiated cells from hPSCs. We generated cardiomyocytes, and endothelial progenitor cells.

Figure 3:
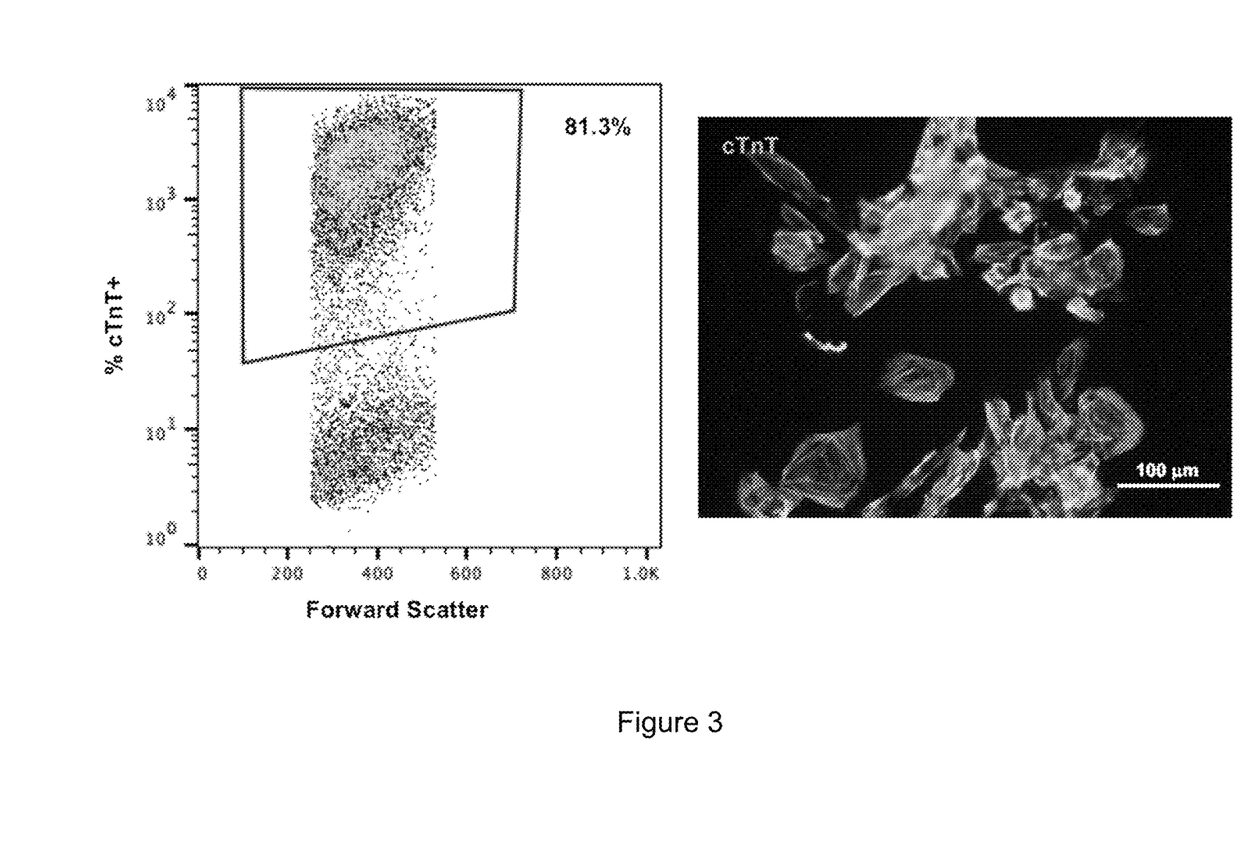
FIG. 3 is a representation of hPSC cultured in PSC Medium and differentiated to cardiomyocytes. The left column shows high purity of cardiac troponin T (cTnT) positive cells (cardiomyocytes) using flow cytometry, and the right column shows staining for cTnT.

Cardiac differentiation: When hPSCs maintained on Matrigel plates achieved confluence, cells were treated with CHIR99021 in RPMI/B27-insulin for 24 h (day 0 to day 1). The medium was changed to RPMI/B27-insulin. On day 3, 5 µM inhibitor for Wnt Production (IWP) 2 or IWP4 was added and removed during the medium change on day 5. Cells were maintained in the RPMI/B27 starting from day 7, with the medium changed every 3 d. Results are shown in FIG. 3. hPSCs were differentiated into cardiomyocytes followed a GiWi protocol. On day 15 of differentiation, differentiated cells were immunostained with cTnT.

Figure 4:
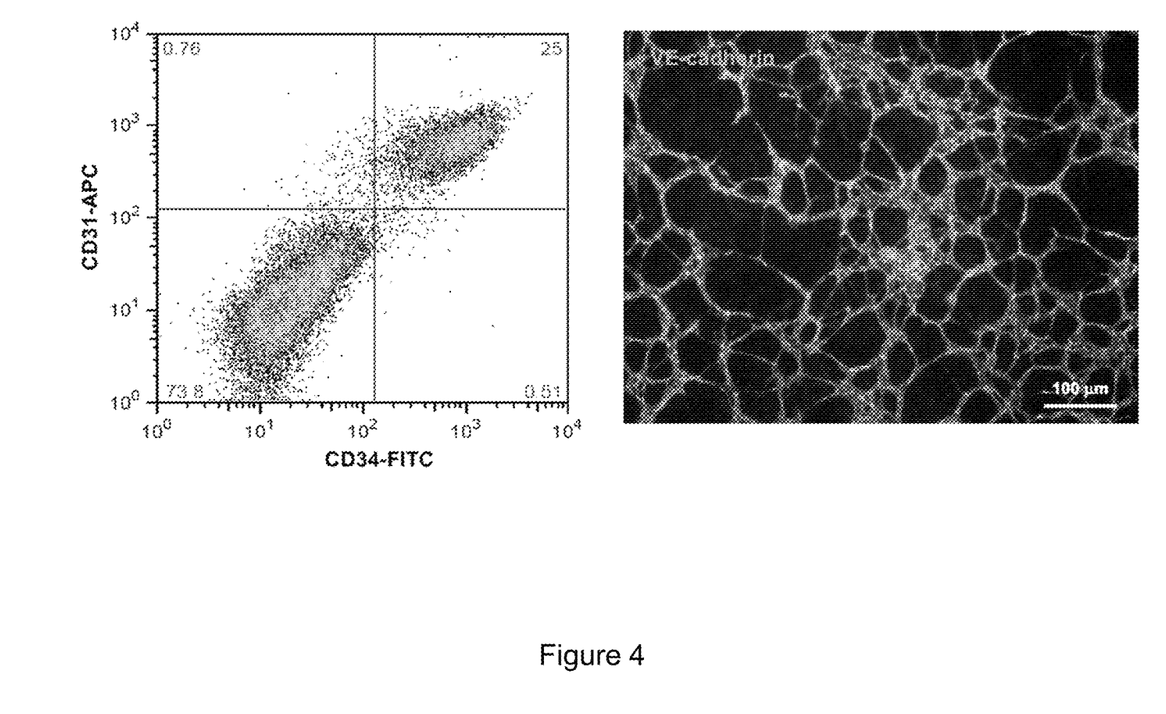
FIG. 4 is a representation of hPSC cultured in PSC Medium and differentiated to endothelial progenitor cells. The left column shows a plot of CD31 versus CD34 and the right column shows staining for VE-cadherin, all markers for endothelial progenitor cells.

Endothelial progenitor cell differentiation: At day 0, hPSCs were treated with 6-10 µM CHIR99021 for 2 days in Advanced DMEM/F12, 2.5 mM GlutaMAX, and 60 µg/ml ascorbic acid phosphate. After 2 days, CHIR99021-containing medium was aspirated and cells were maintained in basal medium without CHIR99021 for 3-4 additional days. Results are shown in FIG. 4. hPSCs were treated with CHIR99021 for two days followed by another 3 days in a defined medium. On day 5 of differentiation, cell were immunostained with VE-cadherin. Cells were also analyzed via flow cytometry for CD31 and CD34 expression.

Example 4

Figure 5:
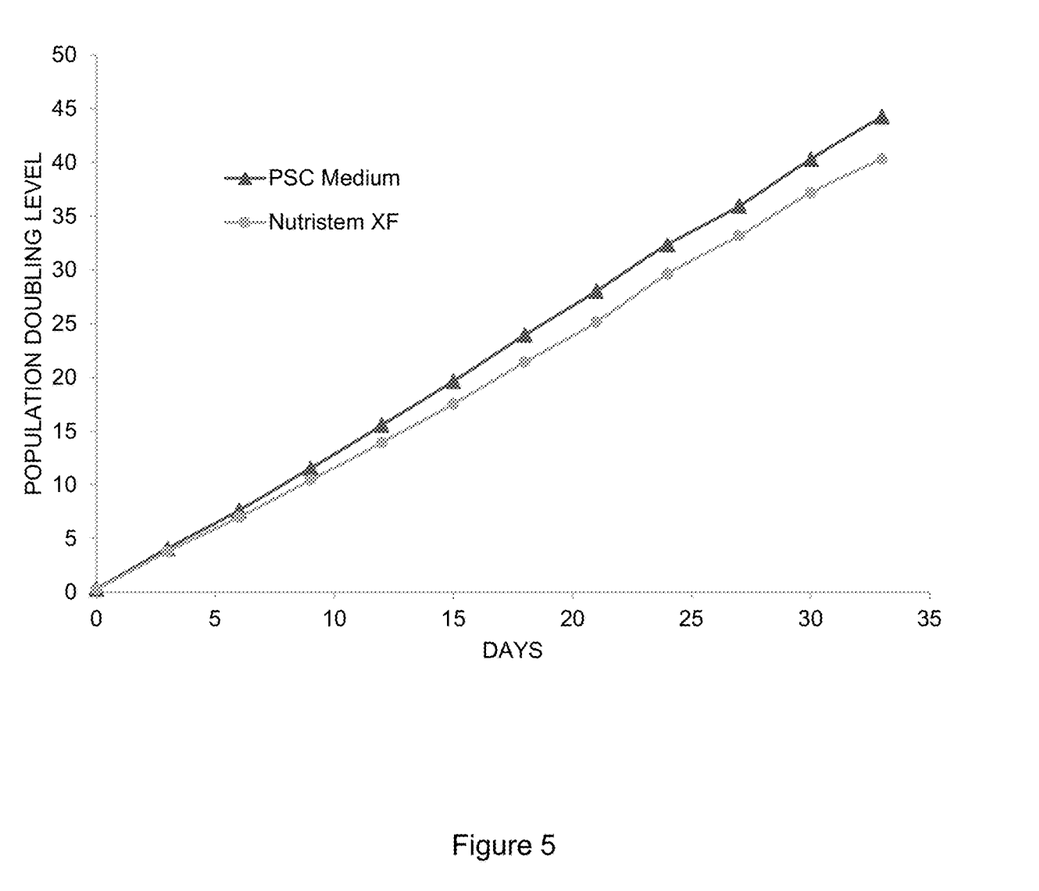
FIG. 5 shows cell growth rate for human embryonic stem cell line HS181 cultured in PSCM compared to Nutristem® XF on laminin-521. Population doubling level is plotted as a function of number of days in culture, showing that cells cultured in PSCM display more than twice the cell count even after 30 days, after the initial adaptation passages up to 5 days that show similar population doubling level in both media.

In this example, the human embryonic stem cell line HS181 was plated on a laminin coating Laminin 521 (Ln 521), used at 5 g/ml and cells were cultured in the present medium containing human serum albumin (and therefore, a xeno-free version) and Nutristem hESC XF. No ROCK inhibitor was used. The seeding density was 30,000 cells/cm2 for HS181 and 50,000 cells/cm2 for iPSC3. Cells were fed daily and passaged every $3^{rd}$ day. Cells were cultured for 10 passages. The cells were observed to grow faster with PSCM compared to Nutristem, especially at later passages. (FIG. 5). Immunostaining for pluripotency factors Oct4, DAPI, and SSEA4 was similar for cells in both media. This example demonstrates the present medium can be used for passaging and maintaining stem cells plated on different substrates.

What is claimed is:

1. A cell culture medium comprising Advanced DMEM/F12, a glutamine source at a concentration from 1 to 5 mM, a source of ascorbic acid in addition to that present in Advanced DMEM/F12, wherein the concentration of ascorbic acid in the culture medium is from 0.1 to 0.8 mM, a member of the FGF superfamily at a concentration from 25 to 75 µg/L, a member of the TGF-beta superfamily of ligands selected from the group consisting of TGF-β1, TGF-β2 and TGF-β3 at a concentration from 0.75 to 2.25 µg/L, wherein the medium allows in vitro passaging of undifferentiated human pluripotent stem cells under serum-free, feeder cell-free conditions for at least 30 passages, and wherein the undifferentiated cells express Oct4, Sox2 and Nanog, and maintain karyotypic stability for the at least 30 passages, wherein the proliferation rate of the human pluripotent stem cells (hPSCs) is at least 1.5 times the proliferation rate of the hPSCs cultured in mTeSR1 under similar culture conditions.

2. The cell culture medium of claim 1, wherein the culture medium does not contain one or more of gamma amino butyric acid (GABA), pipecolic acid (PA), and lithium (Li).

3. The cell culture medium of claim 1, wherein the culture medium does not contain one or more of 2-mercaptoethanol, pluronic F-68, and Tween 80.

4. The cell culture medium of claim 1, wherein the concentration of ascorbic acid in the medium is from 0.1 mM to 0.6 mM.

5. The cell culture medium of claim 4, wherein the concentration of ascorbic acid is from 0.15 to 0.30 mM.

6. The cell culture medium of claim 1, wherein the member of the FGF superfamily is FGF1 or FGF2.

7. The cell culture medium of claim 1, wherein the TGF-beta superfamily of ligands is TGF-β1.

8. The culture medium of claim 1, wherein the glutamine source is L-alanyl-L-glutamine.

9. The cell culture medium of claim 1, wherein the member of the FGF superfamily is from 30 to 70 µg/L, the TGF-β superfamily ligand is from 1.0 to 2.0 µg/L, and glutamine is from 2 to 4 mM.

10. The cell culture medium of claim 9, wherein the ascorbic acid is about 0.25 mM, FGF2 is about 50 µg/L, TGF-beta superfamily ligand is about 1.5 µg/L, and glutamine is about 2.5 mM.

11. The cell culture medium of claim 1, wherein the albumin in the Advanced DMEM/F12 is bovine serum albumin, human serum albumin, or recombinant human or bovine albumin.

12. A cell culture medium comprising the following components

| Component | mg/L |
|---|---|
| L-alanyl glutamine | 543 |
| Ascorbic acid phosphate | 63.5 |
| FGF2 | 0.05 |
| TGFβ1 | 0.0015 |
| Glycine | 18.75 |
| L-Alanine | 4.45 |
| L-Arginine hydrochloride | 147.5 |
| L-Asparagine-$H_2O$ | 7.5 |
| L-Aspartic acid | 6.65 |
| L-Cysteine hydrochloride-$H_2O$ | 17.56 |
| L-Cystine 2HCl | 31.29 |
| L-Glutamic Acid | 7.35 |
| L-Histidine hydrochloride-$H_2O$ | 31.48 |
| L-Isoleucine | 54.47 |
| L-Leucine | 59.05 |
| L-Lysine hydrochloride | 91.25 |
| L-Methionine | 17.24 |
| L-Phenylalanine | 35.48 |
| L-Proline | 17.25 |
| L-Serine | 26.25 |
| L-Threonine | 53.45 |
| L-Tryptophan | 9.02 |
| L-Tyrosine disodium salt dihydrate | 55.79 |
| L-Valine | 52.85 |
| Biotin | 0.0035 |
| Choline chloride | 8.98 |
| D-Calcium pantothenate | 2.24 |
| Folic Acid | 2.65 |
| Niacinamide | 2.02 |
| Pyridoxine hydrochloride | 2 |
| Riboflavin | 0.219 |
| Thiamine hydrochloride | 2.17 |
| Vitamin B12 | 0.68 |
| i-Inositol | 12.6 |
| Calcium Chloride ($CaCl_2$) (anhyd,) | 116.6 |
| Cupric sulfate ($CuSO_4$-$5H_2O$) | 0.0013 |
| Ferric Nitrate ($Fe(NO_3)_3 \cdot 9H_2O$) | 0.05 |
| Ferric sulfate ($FeSO_4$-$7H_2O$) | 0.417 |
| Magnesium Chloride (anhydrous) | 28.64 |
| Magnesium Sulfate ($MgSO_4$) (anhyd,) | 48.84 |
| Potassium Chloride (KCl) | 311.8 |
| Sodium Bicarbonate ($NaHCO_3$) | 2438 |
| Sodium Chloride (NaCl) | 6995.5 |
| Sodium Phosphate dibasic ($Na_2HPO_4$) anhydrous | 71.02 |
| Sodium Phosphate monobasic ($NaH_2PO_4$-$H_2O$) | 62.5 |
| Zinc sulfate ($ZnSO_4$-$7H_2O$) | 0.864 |
| Lipid rich albumin | 400 |
| Transferrin | 7.5 |
| Insulin | 10 |
| Glutathione, monosodium | 1 |
| Ammonium Metavanadate | 3.00E−04 |
| Manganous Chloride | 5.00E−05 |
| Sodium Selenite | 0.005 |
| D-Glucose (Dextrose) | 3151 |
| Ethanolamine | 1.9 |
| Hypoxanthine Na | 2.39 |
| Linoleic Acid | 0.042 |
| Lipoic Acid | 0.105 |
| Phenol Red | 8.1 |
| Putrescine 2HCl | 0.081 |
| Sodium Pyruvate | 110 |
| Thymidine | 0.365 | present at the concentrations indicated ±10%.

13. The cell culture medium of claim 12, wherein the components are present at the concentrations indicated.

14. A method of culturing and maintaining human pluripotent stem cells said method comprising growing the human pluripotent stem cells in the culture medium of claim 1, wherein the human pluripotent stem cells are cultured under serum-free, feeder cell-free, conditioned medium from feeder cells-free conditions for maintaining undifferentiated human pluripotent stem cells.

15. The method of claim 14, wherein the human pluripotent stem cells are not exposed to feeder cells medium or to conditioned medium therefrom.

16. The method of claim 14, wherein the human pluripotent stem cells are maintained in culture for at least 30 passages, and express pluripotency markers at least after 30 passages.

17. The method of claim 14, wherein the human pluripotent stem cells are grown on a substrate.

18. The method of claim 17, wherein the substrate is vitronectin, laminin or matrigel.

19. The method of claim 16, wherein the pluripotency markers are Nanog, Oct4 and/or Sox2.

20. The method of claim 14, wherein the human pluripotent stem cells are human embryonic stem cells or human induced pluripotent stem cells.

21. A kit for preparing a cell culture medium comprising
i) Advanced DMEM/F12;
ii) a mixture comprising ascorbic acid phosphate, L-alanyl-L-glutamine, a member of the FGF superfamily, and a member of the TGF-β superfamily of ligands selected from the group consisting of TGF-β1, TGF-β2 and TGF-β3, wherein the components are provided such that the concentration of the TGF-β superfamily of ligands is from 0.75 to 2.25 µg/L, the concentration of ascorbic acid is from 0.1 to 0.8 mM, the concentration of the FGF superfamily is from 25 to 75 µg/L, and the concentration of L-alanyl-L-glutamine is from 1 to 5 mM, and iii) instructions for preparing the cell culture medium, wherein the cell culture medium prepared according to the instructions in the kit allows in vitro passaging of undifferentiated human pluripotent stem cells (hPSCs) under serum-free, feeder cell-free conditions for at least 30 passages, wherein the proliferation rate of the hPSCs is at least 1.5 times the proliferation rate of the hPSCs cultured in mTeSR1 under similar culture conditions.

22. The kit of claim 21, wherein the member of the FGF superfamily is FGF1 or FGF2, and the member of the TGF-β superfamily of ligands is TGF-β 1.

23. The cell culture medium of claim 1, wherein the proliferation rate of the hPSCs and the expression of pluripotency marker Nanog is at least twice that of hPSCs cultured in mTeSR1 under similar culture conditions.

* * * * *